(12) United States Patent
Spindler

(10) Patent No.: US 10,869,749 B2
(45) Date of Patent: Dec. 22, 2020

(54) REINFORCED GRAFT PROSTHESIS

(71) Applicant: COOK MEDICAL TECHNOLOGIES LLC, Bloomington, IN (US)

(72) Inventor: Ralf Spindler, Solsberry, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 232 days.

(21) Appl. No.: 15/953,951

(22) Filed: Apr. 16, 2018

(65) Prior Publication Data

US 2018/0303597 A1    Oct. 25, 2018

Related U.S. Application Data

(60) Provisional application No. 62/488,275, filed on Apr. 21, 2017.

(51) Int. Cl.
   *A61F 2/07*    (2013.01)
   *B21F 45/00*   (2006.01)
   *A61F 2/89*    (2013.01)

(52) U.S. Cl.
   CPC .............. *A61F 2/07* (2013.01); *B21F 45/008* (2013.01); *A61F 2/89* (2013.01); *A61F 2002/072* (2013.01); *A61F 2210/0076* (2013.01); *A61F 2230/0091* (2013.01); *A61F 2240/001* (2013.01)

(58) Field of Classification Search
   CPC ........ A61F 2/07; A61F 2/89; A61F 2002/072; A61F 2/88; A61F 2210/0076; A61F 2/90; A61F 2230/0091
   See application file for complete search history.

(56) References Cited

U.S. PATENT DOCUMENTS

| | | | |
|---|---|---|---|
| 4,604,762 A * | 8/1986 | Robinson ............... | A61F 2/06 623/1.44 |
| 5,413,598 A | 5/1995 | Moreland | |
| 5,607,478 A | 3/1997 | Lentz et al. | |
| 5,628,788 A | 5/1997 | Pinchuk | |
| 5,976,192 A | 11/1999 | McIntyre et al. | |
| 6,001,123 A | 12/1999 | Lau | |
| 6,334,868 B1 | 1/2002 | Ham | |
| 6,336,937 B1 | 1/2002 | Vonesh et al. | |
| 6,500,204 B1 * | 12/2002 | Igaki ..................... | A61F 2/90 623/1.18 |

(Continued)

FOREIGN PATENT DOCUMENTS

| EP | 2499997 | 9/2012 |
|---|---|---|
| WO | WO9526695 | 10/1995 |

OTHER PUBLICATIONS

Extended European Search Report for 18275050.5 dated Oct. 12, 2018, 8 pgs.

(Continued)

*Primary Examiner* — Katherine M Shi

(74) *Attorney, Agent, or Firm* — Brinks Gilson & Lione

(57) ABSTRACT

A medical device, such as a prosthesis, and method of forming the same are disclosed. The medical device includes a cover material and a reinforcement element, and may include a stent frame structure. The reinforcement element includes a plurality of bends disposed about a pattern axis. The pattern axis is arranged helically along the cover material.

20 Claims, 8 Drawing Sheets

(56) References Cited

U.S. PATENT DOCUMENTS

| | | |
|---|---|---|
| 6,592,614 B2 | 7/2003 | Lenker et al. |
| 6,613,072 B2 | 9/2003 | Lau et al. |
| 6,800,089 B1 | 10/2004 | Wang |
| 6,863,686 B2 | 3/2005 | Shannon et al. |
| 6,911,040 B2 | 6/2005 | Johnson et al. |
| 7,118,592 B1 | 10/2006 | Dang et al. |
| 7,413,573 B2 | 8/2008 | Hartley et al. |
| 7,879,085 B2 | 2/2011 | Sowinski et al. |
| 8,048,143 B2 | 11/2011 | Shaw |
| 8,262,979 B2 | 9/2012 | Anneaux et al. |
| 8,721,704 B2 | 5/2014 | Cully et al. |
| 9,017,350 B2 | 4/2015 | Karabey et al. |
| 2002/0007212 A1* | 1/2002 | Brown .................. A61F 2/91 623/1.16 |
| 2002/0096252 A1 | 7/2002 | Lukic |
| 2002/0156523 A1 | 10/2002 | Lau et al. |
| 2004/0167606 A1 | 8/2004 | Chouinard |
| 2005/0131519 A1 | 6/2005 | Hartley |
| 2005/0171597 A1 | 8/2005 | Boatman et al. |
| 2006/0253190 A1* | 11/2006 | Kuo .................. A61F 2/07 623/1.44 |
| 2007/0021707 A1 | 1/2007 | Caro et al. |
| 2009/0125095 A1* | 5/2009 | Bui .................. A61F 2/07 623/1.13 |
| 2010/0324650 A1 | 12/2010 | Keeble et al. |
| 2011/0009951 A1* | 1/2011 | Bogert .................. A61F 2/88 623/1.22 |
| 2013/0053961 A1 | 2/2013 | Derwin et al. |
| 2013/0238086 A1 | 9/2013 | Ballard et al. |
| 2015/0005869 A1 | 1/2015 | Soletti et al. |
| 2016/0262868 A1 | 9/2016 | Soletti et al. |

OTHER PUBLICATIONS

Invitation pursuant to Rule 62a(1) EPC for EP18275050.5 dated Aug. 21, 2018, 2 pgs.

* cited by examiner

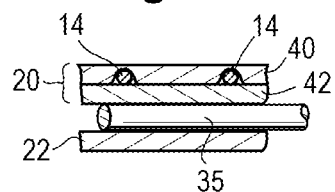 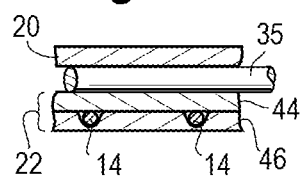 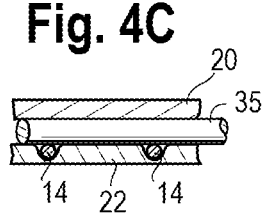
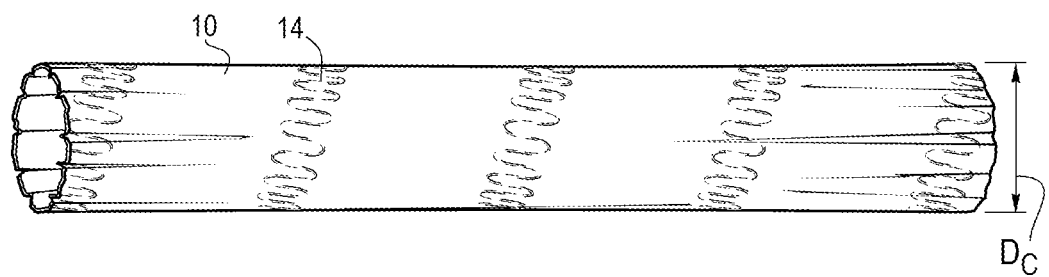
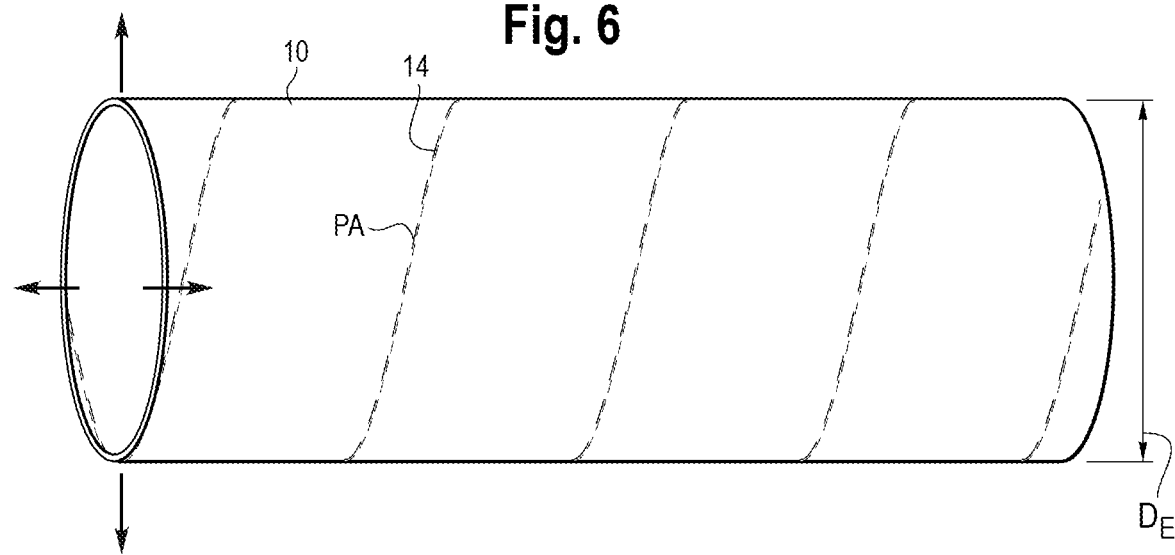

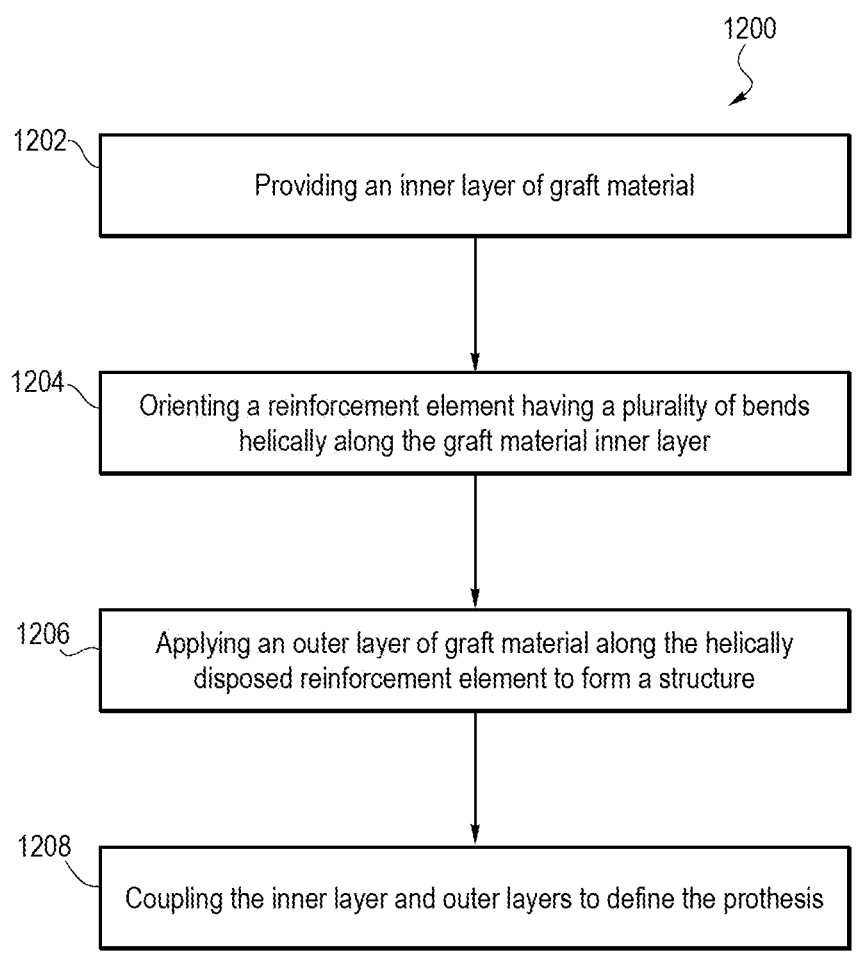

US 10,869,749 B2

REINFORCED GRAFT PROSTHESIS

PRIORITY CLAIM

This invention claims the benefit of priority of U.S. Provisional Application Ser. No. 62/488,275, entitled "Reinforced Graft Prosthesis," filed Apr. 21, 2017, the disclosure of which is hereby incorporated by reference in its entirety.

BACKGROUND

The present disclosure relates generally to medical devices, and particularly, to endoluminal prostheses, stent-grafts, or grafts with a reinforcement element associated with the graft material and methods for the manufacture and use of the same for repair of damaged vessels, ducts, or other physiological pathways.

Various interventions have been provided for weakened, aneurysmal, dissected or ruptured vessels, including surgical interventions and endovascular interventions. Endovascular interventions generally include inserting an endoluminal device or prosthesis such as a stent or stent graft into the damaged or diseased body lumen to provide support for the lumen, and to exclude damaged portions thereof. Such prosthetic devices are typically positioned at the point of treatment or target site by navigation through the vessel, and possibly other connected branch vessels, until the point of treatment is reached. This navigation may require the device to be able to move axially through the vessel(s) prior to deployment, while still maintaining the ability to exert an outward force on the interior wall once deployed.

In the field of aortic interventions, endoluminal devices are placed in vessels to address and correct diseased tissue resulting from atherosclerotic plaques, aneurysm or weakening of body vessel walls, and arterial dissection. In the case of atherosclerosis, plaque buildup results in narrowing of the vessel which may lead to reduced or blocked blood flow within the body vessel. Endoluminal devices for atherosclerosis act to radially expand the narrowed area of the body vessel to restore normal blood flow. In the case of an aneurysm, a weakening of the body vessel wall results in ballooning of the body vessel which can eventually lead to rupture and subsequent blood loss. In some cases, the aneurysmal sac may include plaque. Endoluminal devices for aneurysms act to seal off the weakened area of the body vessel to reduce the likelihood of the body vessel rupture. In the case of arterial dissection, a section of the innermost layer of the arterial wall is torn or damaged, allowing blood to enter a false lumen divided by the flap between the inner and outer layers of the body vessel. The growth of the false lumen may eventually lead to complete occlusion of the actual artery lumen. Endoluminal devices for dissection healing would reappose the dissection flap against the body vessel wall to close it off and restore blood flow through the true lumen.

After such endoluminal device placement for the various aortic interventions, graft creep may occur, which may be caused by graft material fatigue under repetitive blood pressure pulsations and body vessel movements, as well as the loading properties of the graft material. If the graft and/or stent is not dilated to the maximum diameter, the diameter of the device may increase over time up to the maximum diameter of the device. While some graft creep may be acceptable, extreme graft creep may eventually lead to graft creep rupture resulting in radial and/or longitudinal splits in the graft material, thereby leading to endoleaks, aneurysms, degenerative changes, calcification or other conditions.

SUMMARY

In one example, a prosthesis includes a radially expandable stent frame structure, a cover material disposed along the stent frame structure, and a reinforcement element coupled to the cover material. The reinforcement element includes a plurality of bends disposed about a pattern axis, and the pattern axis arranged helically along the cover material.

In another example, a medical device includes a covering material having an outer layer and an inner layer; and a reinforcement element disposed within the covering material. The reinforcement element includes a plurality of bends. The reinforcement element is disposed along a pattern axis helically disposed about the inner layer. The plurality of bends of the reinforcement element is disposed generally in an undulating pattern about the pattern axis. At least one of the plurality of bends forms each undulation of the undulating pattern.

In another example, a method of forming a prosthesis is provided. The method including one or more of the following steps. A step includes providing an inner layer of graft material. A step includes orienting a reinforcement element having a plurality of bends helically along the graft material inner layer. A step includes applying an outer layer of graft material along the helically disposed reinforcement element. A step includes coupling the inner layer and outer layers to define the prosthesis.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 4A-4C are magnified cross-sectional views of the graft covering.

FIG. 5 is a perspective view of an example of a medical device compressed or crimped at its crimped diameter with a reinforcement element.

FIG. 6 is a perspective view of an example of a medical device over-expanded beyond its nominal diameter with a reinforcement element.

FIG. 12 is a flow diagram, depicting a method of making a medical device.

DETAILED DESCRIPTION OF THE PREFERRED EMBODIMENTS

Medical devices for implantation or for deployment within a human or animal body for repair of damaged vessels, ducts, or other physiological pathways are provided. The medical devices have a graft covering with a reinforcement element configured and oriented to withstand and inhibit creep rupture, while still achieving other desirable properties of the medical device such as, for example, longitudinal bending flexibility and low profile for delivery within a small as possible French sized catheter. Creep within the graft material may cause thinning of the graft material wall. The potential for creep rupture due to the thinning of the graft wall in combination with the longitudinal bending of the device with the thinned graft wall may be further reduced with the reinforcement element associated with the graft covering.

In the present application, the term "proximal end" is used when referring to that end of a medical device closest to the heart after placement in the human body of the patient, and may also be referred to as inflow end (the end that receives fluid first), and the term "distal end" is used when referring to that end opposite the proximal end, or the one farther from the heart after its placement, and may also be referred to as the outflow end (that end from which fluid exits).

Medical devices may be any devices that are introduced temporarily or permanently into the body for the prophylaxis or therapy of a medical condition. For example, such medical devices may include, but are not limited to: endovascular grafts, stent grafts, bifurcated stent grafts or assembly of a multicomponent prosthesis, balloon catheters, meshes, vascular grafts, stent-graft composites, filters (for example, vena cava filters), vascular implants, tissue scaffolds, myocardial plugs, valves (for example, venous valves), various types of dressings, endoluminal prostheses, vascular supports, or other known biocompatible devices.

Figure 1:
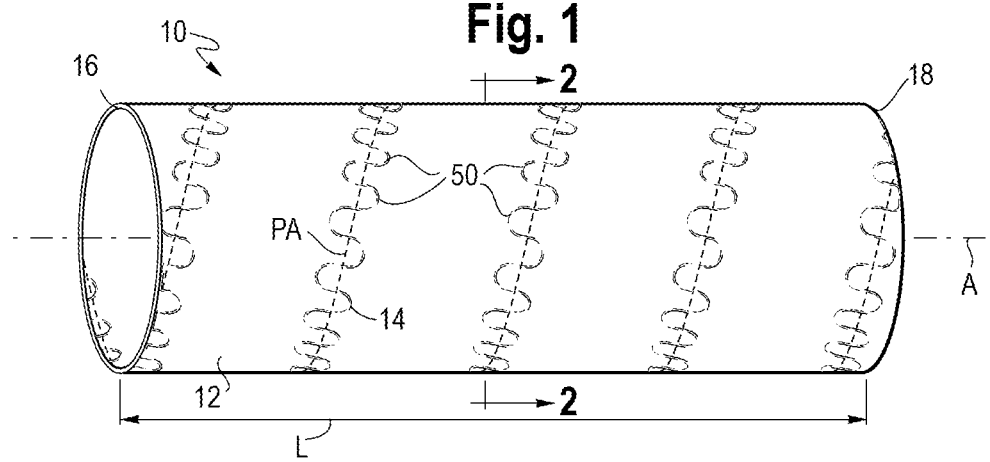
FIG. 1 is a perspective view of an example of a medical device expanded at its nominal diameter with a reinforcement element.

Now looking more closely at the drawings, FIG. 1 depicts one example of a medical device 10, including a tubular graft covering 12 and a reinforcement element 14. The graft covering 12 may be cylindrical having a nominal expanded diameter ($D_N$) along the entire longitudinal length L. It is contemplated the graft covering 12 may have segments that are tapered. In one example, the device 10 is suitable for placement into an aorta and engaging against the aorta. The medical device includes a proximal end 16 and a distal end 18 and is disposed longitudinally about a longitudinal axis A.

Figure 2:
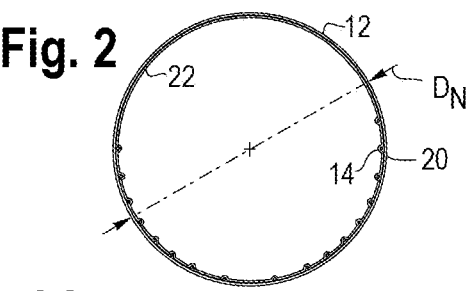
FIG. 2 is transverse cross-sectional view of the medical device in FIG. 1, taken along lines 2-2 in FIG. 1.

The graft covering 12 may include multiple layers. In one example shown in FIG. 2, the graft covering 12 includes a first, outer layer 20 and a second, inner layer 22 bonded to one another, as known in the art. Shown captured between the first layer 20 and the second layer 22 is the reinforcement element 14, although the reinforcement element 14 may be disposed along the outside of the first layer 20 or the inside of the second layer 22. In one example, the second layer 22 is tubular and fitted over a mandrel. The reinforcement element 14 is applied over the inner layer 22 in one of the disclosed patterns. The first layer 20 is applied coaxially over the reinforcement layer 14 and the second layer 22, where the layers 20, 22 are configured for bonding to one another when heat and/or pressure suitable for such bonding is applied.

Figure 3A:
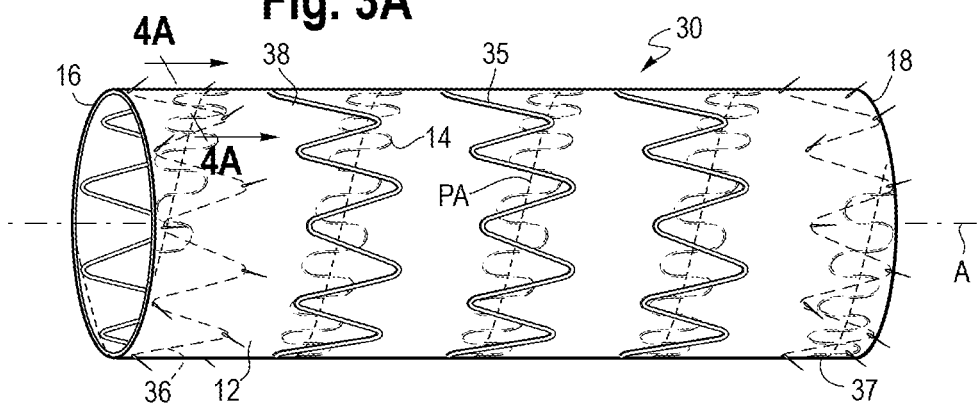
FIG. 3A is a perspective view of another example of a medical device expanded at its nominal diameter with a reinforcement element.

FIG. 3A depicts another example of a medical device 30, which is a modified version of the medical device 10, and as a result will utilize the same reference numerals associated with the medical device 10 for similar components. Medical device 30 includes a stent frame structure 35, in addition to the tubular graft 30 covering 12 and the reinforcement element 14. The stent frame structure 35 may include a single structure or a plurality of structures, such as shown as a series of Z stents axially disposed away from one another about the longitudinal axis. The plurality of stents each form a dosed shape when viewed in a direction substantially orthogonal relative to the main longitudinal axis of the cover material. The stents may be disposed along the inner surface of the graft covering 12 and/or the outer surface of the graft covering 12, as shown. In one example, a proximal internal stent 36 and a distal internal stent 37 are disposed along the proximal and distal ends 16, 18, respectively, and a series of body stents 38 are disposed along the outside of the graft body. The internal stents 36, 37 provides a smooth external prosthesis surface to help seal the respective ends of the main vessel prosthesis against an adjoining vascular wall or against an interconnecting module. Stents 36, 37, 38 may include any suitable stent configuration known in the art. The stents 36, 37, 38 may be balloon-expandable or self-expanding. For example, stents 36, 37, 38 may comprise self-expanding Z stents. The prosthesis may comprise a combination of stents 36, 37, 38 or a single stent having both balloon-expandable and self-expanding properties. The internal stents 36, 37 may comprise radially disposed barbs 39 that extend through the graft material 12 to engage the surrounding vessel wall, thereby anchoring the device to the vessel and preventing migration of the device once it is deployed.

Figure 3B:
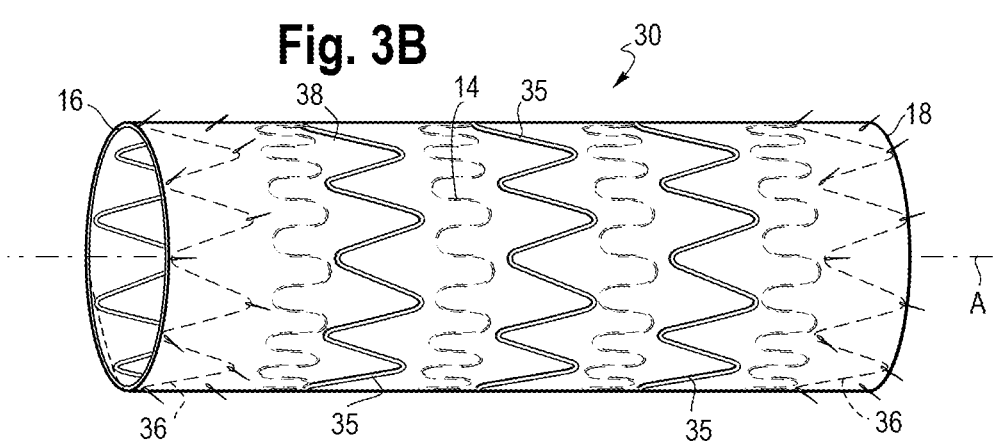
FIG. 3B is a perspective view of another example of a medical device expanded at its nominal diameter with a reinforcement element disposed between adjacent stent members.

The reinforcement element 14 may be located along the medical device to strengthen or support unstented cover material regions between the adjacent stents. FIG. 3B depicts the medical device 30 including the reinforcement element 14 disposed in a pattern between adjacent stents 35, 36. In one example, the reinforcement element 14 may be disposed in a pattern only between stents 35, 36 and not around the stents. In another example, the reinforcement element 14 may be disposed in a pattern between stents 35, 36 and around the stents.

The stent frame structure 35 may be disposed between layers of the tubular graft covering 12. These layers may be same as the first and second layers 20, 22, or different layers, such as, for example, the first layer 20 and a different layer, the second layer 22 and a different layer, or layers different than the first and second layers 20, 22. In one example shown in FIG. 4A, the stent frame structure 35 is captured between the first layer 20 and the second layer 22. The first outer layer 20 is shown including at least two microlayers 40, 42, where the reinforcement element 14 is disposed between the microlayers 40, 42 of the first layer. In another example shown in FIG. 4B, the stent frame structure 35 is captured between the first layer 20 and the second layer 22. The second inner layer 22 includes at least two microlayers 44, 46 as shown, where the reinforcement element 14 is disposed between the microlayers 44, 46 of the second layer. In these examples, at least one microlayer separates the reinforcement element 14 and the stent frame structure 35. In the next example, the reinforcement element 14 and the stent frame structure 35 may be in contacting relationship. In another example shown in FIG. 4C, the stent frame structure 35 is captured between the first layer 20 and the second layer 22. The reinforcement element 14 is also disposed between the first and second layers 20, 22. The reinforcement element 14 may be disposed along the inside of the stent frame structure 35, as shown, or along the outside of the stent frame structure 35. Any of the layers that are shown as a single layer may include a multi-microlayer configuration. In one example, the second layer or microlayer of the first layer is tubular and fitted over a mandrel. Depending on the configuration, the reinforcement element 14 and/or stent frame structure 35 is applied over the second layer or the microlayer in one of the disclosed patterns. The first layer or another microlayer is applied over the reinforcement element 14 and/or the stent frame structure to form a construct reading for bonding when heat and/or pressure are applied.

In FIGS. 1 and 3, the reinforcement element 14 is coupled to the graft covering 12 along a pattern axis PA. The reinforcement element 14 is capable of undergoing several changes in configurations, as will be described, as the medical device 10 or 30 is crimped into a low profile diameter (Dc) (as shown in FIG. 5) and loaded onto a delivery catheter, radially expanded from the low profile diameter Dc to the nominal diameter $D_N$, longitudinally bent due to body vessel movement, and undergoes graft creep during implantation, resulting in an over-expanded diameter (De) (as depicted in FIG. 6). In one example, the reinforcement element 14 is shown including a plurality of bends 50 disposed about the pattern axis PA. The term "bends" is used to define the element shaped having various changes in directions about the pattern axis PA (that is, one wavelength about the axis equaling two bends), such as, for the example, the bend shape may have one or any combination of a sinusoidal shape, square shape, sawtooth or triangular angular shape, or other known bend shapes, at common or different frequencies and/or amplitudes relative to the pattern axis PA.

Figure 7A:
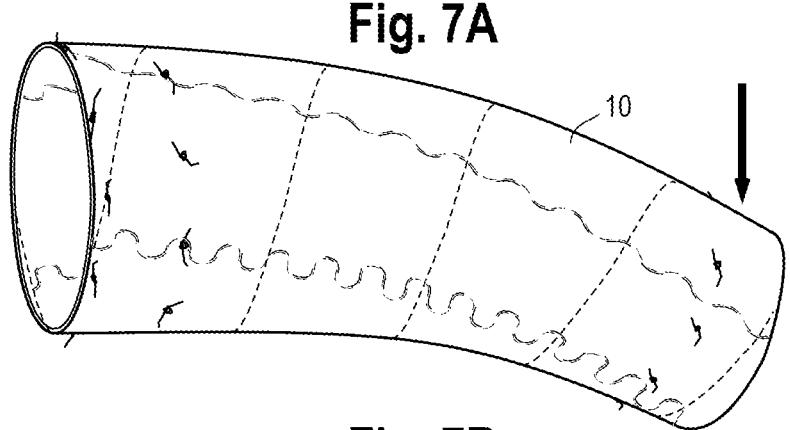
FIG. 7A depicts another example of a medical device with a reinforcement element in a long helical pattern under a moment load.
Figure 7B:
FIG. 7B depicts the medical device in FIG. 1 under a moment load.

The reinforcement element 14 may be disposed circumferentially and/or longitudinally along the graft covering 12. The circumferential aspect of the reinforcement element pattern may provide reinforcing support and hoop strength to inhibit graft creep in the radial direction (see FIG. 6). The longitudinal aspect of the reinforcement element pattern may provide tensile strength to the graft covering during longitudinal bending, as shown in FIGS. 7A-7B. To this end, the reinforcement element under the tensile load along the top of the device may become more straightened (that is, smaller amplitude) than the reinforcement element under the compressive load along the bottom of the device. In one example, the reinforcement element 14 is disposed in circumferentially and longitudinally along the graft covering. FIG. 7A depicts the pattern axis of the device in a helical configuration in a more longitudinal than radial orientation (that is, the pattern axis is more parallel to the longitudinal axis) than in the device shown in FIG. 7B.

Figure 8:
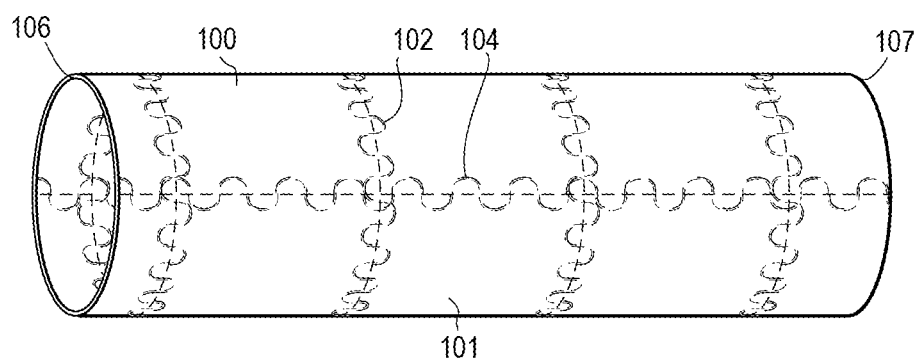
FIG. 8 is a perspective view of another example of a medical device expanded at its nominal diameter with a reinforcement element.
Figure 9:
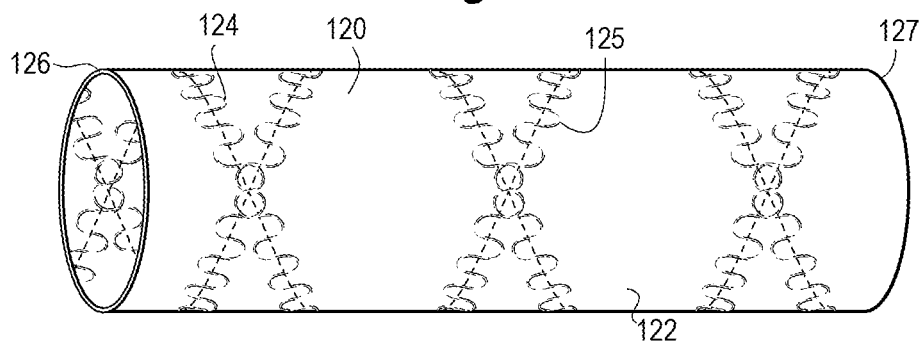
FIG. 9 is a perspective view of another example of a medical device expanded at its nominal diameter with a reinforcement element.

FIGS. 1 and 3 show the reinforcement element 14 disposed along the pattern axis PA that is helically disposed along the graft covering 12. The reinforcement element 14 may include a single strand of one or more bundled filaments. In one example, the reinforcement element 14 is a single strand configured to have a plurality of bends 50 and disposed helically along the graft covering 12. In another example, the reinforcement element 14 may include multiple strands. FIG. 8 depicts an alternative medical device 100 with multiple strands associated with the graft covering 101, including one or more reinforcement elements 102 in the shape of annular members and/or one or more reinforcement elements 104 extending longitudinally between the proximal and distal ends 106, 107. FIG. 9 depicts an alternative medical device 120 with multiple strands associated with the graft covering 122, including one or more reinforcement elements 124 in a helical shape going in a first direction, for example toward the proximal end 126, and/or one or more reinforcement elements 125 in a helical shape going in a second direction, for example toward the distal end 127. In another example, the reinforcement element 14 in FIG. 1 or 3 may include multiple strands that make up the helical pattern shown. Other patterns are contemplated that provide hoop and tensile strength to the graft covering. In examples with multiple reinforcement elements, each reinforcement element may have the same configuration and material. In other examples, a first reinforcement element may have a first configuration and a second reinforcement element may have a second configuration different from the first configuration, either from the same material or different materials. At least a partial number of the multiple reinforcement elements may be connected at the intersections of the strands to form a yarn mesh.

Figure 10A:
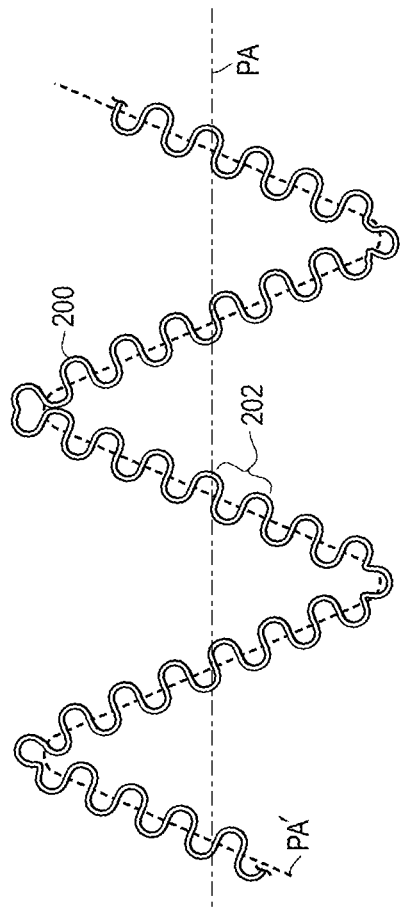
FIGS. 10A-10C illustrate the change in configuration of a reinforcement element of the medical device from its crimped diameter, nominal diameter and over-expanded diameter.
Figure 10B:
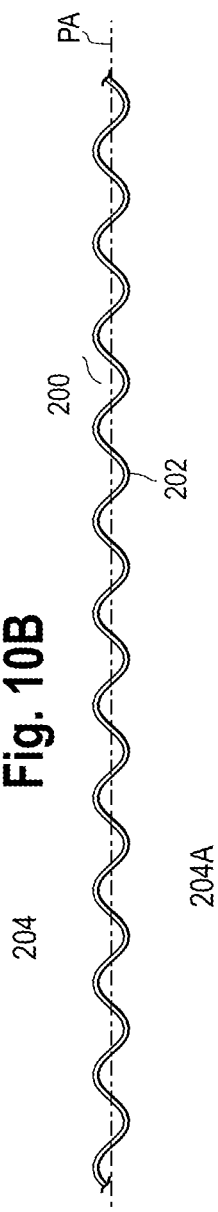
Figure 10C:

As mentioned previously, the reinforcement element (now referred to as 200) is capable of undergoing several changes in configurations. FIGS. 10A-10C illustrate different reinforcement element configurations. The reinforcement element 200 in its stretched extended configuration in this illustration prior to being applied is about twice the longitudinal length L of the medical device. FIG. 10B depicts the state of the reinforcement element 200 when the medical device is radially expanded to a nominal diameter $D_N$. The plurality of bends 202 of the reinforcement element 200 are disposed generally in an undulating pattern 204 about the pattern axis PA, with one of the plurality of bends 202 forming each undulation 204A of the undulating pattern 204. The reinforcement element in FIG. 10B may include a first spatial frequency in terms of an X number of bends per linear length of the pattern axis. The X number of bends per linear length may be less than 1 bend/1 mm. The first spatial frequency may be suitable to permit greater longitudinal bending flexibility for the medical device than previously known as the bends in the reinforcement element may allow some stretching of the graft covering. FIG. 10A depicts the state of the reinforcement element 200 when the medical device is radially compressed in a low profile to a compressed diameter Dc. The reinforcement element 200 may include a second spatial frequency in terms of a Y number of bends per linear length of the pattern axis. The Y number of bends per linear length may be selected from the range of 2 bends/1 mm to 1 bend/2 mm, and in one example, 1 bend/1 mm. The second spatial frequency is greater than or has a higher bend density than the first spatial frequency. The graft covering when crimped may be bunched with creases and folds to permit the higher density of bends. In this state, the bends 202 are shown disposed about a second axis PA' that is also in an undulating pattern about the pattern axis PA, such as the axis PA' has an axis spatial frequency selected from the range of 1 bends/4 mm to 1 bend/6 mm, and in one example, 1 bend/5 mm. During expansion to the nominal diameter $D_N$, the second axis PA' and the pattern axis PA become aligned, resulting the configuration shown in FIG. 10B.

FIG. 10C depicts the state of the reinforcement element 200 when the medical device is radially expanded to an over-expanded diameter $D_E$ that is greater than the nominal diameter $D_N$. The over-expansion (shown by the arrows w in FIG. 6) may be due to graft creep. The reinforcement element 200 takes on a more linear shape without any bends 202, that is, bends difficult to measure and determined. The tensile strength of the reinforcement element 200 in the linear shape strengthens the tensile strength and hoop strength of the graft covering to inhibit further graft creep and maintain longitudinal bending flexibility.

Figure 11A:
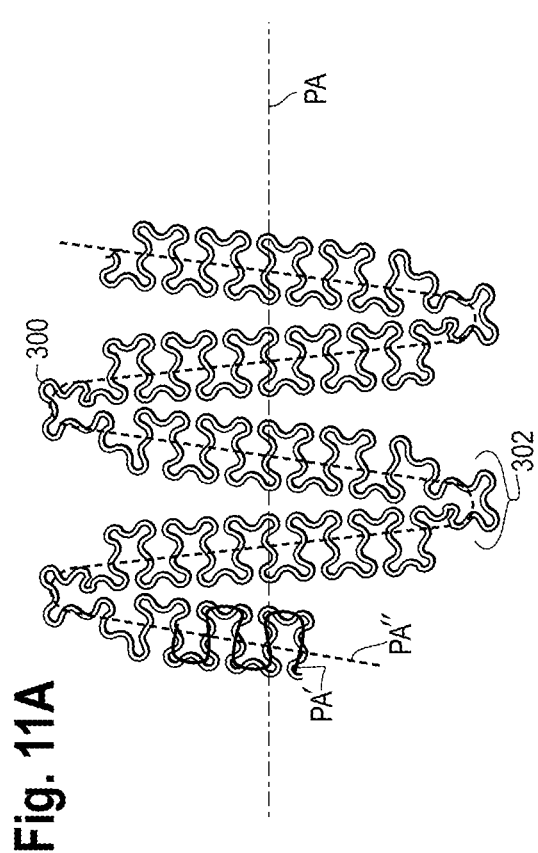
FIGS. 11A-11D illustrate the change in configuration of a reinforcement element of the medical device from its crimped diameter, nominal diameter, transition diameter and over-expanded diameter.
Figure 11B:
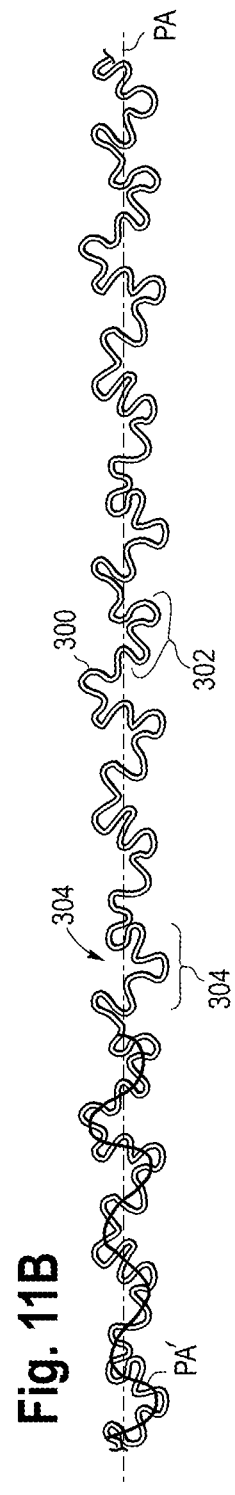

FIGS. 11A-11D illustrate different reinforcement element configurations, now referred to as reinforcement element 300. The reinforcement element 300 in its stretched extended configuration prior to being applied is about four times the longitudinal length L of the medical device. FIG. 11B depicts the state of the reinforcement element 300 when the medical device is radially expanded to a nominal diameter $D_N$. The reinforcement element 300 may include a first spatial frequency in terms of an X' number of bends per linear length of the pattern axis. The X' number of bends per linear length may be selected from the range of may be suitable to permit greater longitudinal bending flexibility for the medical device than previously known as the bends 302 in the reinforcement element 300 may allow stretching of the graft covering. The X' number of bends per linear length may be less than 5 bends/2 mm. The plurality of bends 302 of the reinforcement element 300 is disposed generally in an undulating pattern 304 about the pattern axis PA, with two or more of the plurality of bends 302, for example, two or three bends, forming each undulation 304A of the undulating pattern 304. In this state, the bends 302 may also be disposed about the second axis PA' that is shown in an undulating pattern about the pattern axis PA.

Figure 11C:
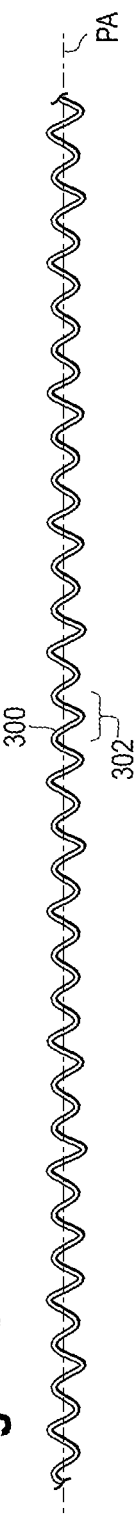

FIG. 11A depicts the state of the reinforcement element 300 when the medical device is radially compressed in a low profile to a compressed diameter Dc. The reinforcement element 300 includes a Y' number of bends 302 per linear length of the pattern axis PA. The Y' number of bends per linear length is greater than or has a higher bend density than the X' number. The Y' number of bends per linear length may be selected from the range of 2 bends/1 mm to 5 bends/1 mm, and in one example, 5 bends/2 mm. In this state, the second pattern axis PA' is shown in an undulating pattern about the third axis PA", that is in an undulating pattern about the pattern axis PA. The second pattern axis PA' has an axis spatial frequency selected from the range of 1 bend/2 mm to 3 bends/2 mm, and in one example, 2 bends/3 mm. The third pattern axis P"' has an axis spatial frequency selected from the range of 1 bends/8 mm to 1 bend/12 mm, and in one example, 1 bend/10 mm. During expansion to the nominal diameter $D_N$, the third axis PA" and the pattern axis PA become aligned, resulting the configuration shown in FIG. 11B. FIG. 11C depicts the state of the reinforcement element 300 when the medical device is radially expanded to a diameter greater than the nominal diameter $D_N$. The reinforcement element includes a Z' number of bends 302 per linear length of the pattern axis PA, which is less than or has a lower bend density than the X' number. The Z' number of bends per linear length may be less than 1 bend/1 mm. During expansion to the diameter De, the second axis PA' and the pattern axis PA become aligned, resulting the configuration shown in FIG. 11D.

Figure 11D:

FIG. 11D depicts the state of the reinforcement element 400 in a more linear form when the medical device is radially expanded to an over-expanded diameter $D_E$ that is greater than the nominal diameter $D_N$ and the diameter that would result in the configuration in FIG. 11C. The over expansion may be due to graft creep. The reinforcement element 300 takes on a more linear shape without any bends 302 or bends difficult to measure and determined. The tensile strength of the reinforcement element 300 in the linear shape strengthens the graft covering to inhibit further graft creep and maintain longitudinal bending flexibility.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material may include a biocompatible synthetic or biomaterial. Examples of suitable synthetic materials include fabrics, woven and nonwoven materials, and porous and nonporous sheet materials. Other synthetic graft materials include biocompatible materials such as polyester, polytetrafluoroethylene ("PTFE"), polyurethane ("PU"), fluorinated ethylene propylene ("FEP") and the like. Examples of suitable biocompatible materials include, for example, pericardial tissue and extracellular matrix materials ("ECMM") such as SIS.

Other synthetic materials, such as biocompatible synthetic materials, may be used for the graft material. Synthetic materials may include polymers such as, for example, poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly (methacrylic acid), polylactides ("PLA"), polyglycolides ("PGA"), poly(lactide-co-glycolid-es) ("PLGA"), polyanhydrides, polyorthoesters or any other similar synthetic polymers that may be developed that are biocompatible. Biocompatible synthetic polymers also may include copolymers, blends, or any other combinations of the forgoing materials either together or with other polymers generally. The use of these polymers will depend on given applications and specifications required. Suitable polymer material may include, for example, polyester such as DACRON™, polyetherurethanes such as THORALON® from Thoratec Corporation (Pleasanton, Calif.), or polyethylene terephthalate ("PET").

In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. The porous sheet may be made of one or more polymers that do not require treatment or modification to be biocompatible.

The graft material, the coating, or one class of materials for electrospinning may also include extracellular matrix materials. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues.

The stent or support frame structures may be any device or structure that provides or is configured to provide rigidity, expansion force, or support to a body part, for example, a diseased, damaged, or otherwise compromised body lumen. Such stent frame structure may include any suitable biocompatible material, including, but not limited to fabrics, metals, plastics, and the like. Examples of suitable materials include metals such as stainless steel and nitinol, and plastics such as PET, PTFE and polyurethane. The stent frame structure may be "expandable," that is, it may be capable of being expanded to a larger-dimension configuration. The stent frame structure may expand by virtue of its own resilience (i.e., self-expanding), upon the application of an external force (i.e., balloon-expandable), or by a combination of both. In one example, the stent frame structure may have one or more self-expanding portions and one or more balloon-expandable portions. The stent struts that are interconnected to one another represents specific configurations of a wire member that comprises a basic structural component of the stent. As used herein, the term "wire" refers to any filamentary member, including, but not limited to, drawn wire and filaments that have been laser cut from a cannula. For example, the stent architecture with the intricate mating elements that form the interlocking joints may lend itself to being manufactured from a metal cannula laser cut to the desired pattern as described. The shape, size, and dimensions of the stent structure may vary. The size of these components and the overall stent structure is determined primarily by the diameter of the vessel lumen at the intended implant site, as well as the desired length of the overall stent device. The stent structure and/or ring structures may have a common cross-sectional area along the body or may vary to have different cross-sectional areas.

Any one of the reinforcement elements described herein may be any structure that provides or is configured to inhibit graft creep in the radial direction and/or provide tensile strength to the graft covering during longitudinal bending. The reinforcement element may be a filament or yarn of any one or more of the disclosed materials listed above with respect to the graft and/or stent frame structure. The filament or yarn may be metal or metal alloy, polymer, and/or textile.

In one example, the reinforcement element comprises PET, and in another example, comprises PET 40 denier yarn.

In one example, the reinforcement element may be prepared by wrapping a reinforcement element material, such as, for example, a heat settable material, for example, PET 40 Denier yarn, around a mandrel in a coiled manner. The mandrel may have a desired diameter, such as for example, 0.46 mm, 1.19 mm, or 1.86 mm. Other mandrel diameters may be selected. The coiled PET yarn is baked in an oven at a baking temperature, such as, for example, 130 deg. C., for a baking period, such as, for example, about 30 minutes. The reinforcement element may be provided preconfigured with the coiled shape. In another example, the reinforcement element may be formed in a serpentine manner without coiling by using a plate with posts and undulating the PET yarn around the posts.

FIG. 12 depicts one example of a method 1200 of forming a medical device. As described above, an inner layer, either single or a plurality of microlayers, of graft material may be provided (step 1202), such as, for example, by wrapping around or sliding over in tubular form over along a mandrel. Any of the layers may further be comprised of microlayers. Any one of the disclosed reinforcement elements in the coiled shape as described above with the plurality of bends may be wrapped or wound around circumferentially and/or longitudinally along the inner layer along a predetermined pattern axis, such as, for example, along a helical pattern axis (step 1204). In another example, the reinforcement element in the coiled shape as described above may be wrapped around circumferentially and/or longitudinally along a tie material prior to applying the tie material to the inner layer. The tie material is configured to securely fix the orientation and pattern of the reinforcement element and to further ease handling of the coiled structure. The tie materials may include, for example, polymer sheets or strips of PU and/or FEP. The length of the reinforcement element may depend on the nominal diameter of the medical device and the nominal length. In one example, the reinforcement element length prior to being applied is about 2 to 6 times the longitudinal length L of the medical device. In another example, the length is about 2 to 4 times the longitudinal length L. As described above, one or more of the plurality of bends of the reinforcement element may form each undulation of the undulating pattern.

An outer layer is disposed along the inner layer to sandwich the reinforcement element between the layers (step 1206). The outer layer is coupled to the inner layer (step 1208) capturing the reinforcement element therebetween and to define the prosthesis. In one example, the outer layer is coupled to the inner layer by bonding. The outer layer facilitates the substantial flattening of the coiled reinforcement element to more of a sinusoidal shape with the plurality of bends. Substantial flattening a three-dimensional structure having portions overlapping, such as a coiled member, is defined as compressing a three-dimensional structure that are not geometrically flat but more compressed than in its natural uncompressed state. The setup configuration is baked or heated in an oven at a baking temperature and/or pressure and a baking period selected based on the layer materials for bonding the layers to one another. The outer layer and the inner layer may be coupled to one another, such as by stitching the layers together, adhesively attaching the layers, or otherwise mechanically attaching the layers to one another. When a stent frame structure is employed, the stent frame structure may be placed beneath or over the reinforcement element prior applying the outer layer and prior to baking. In one example, the inner layer and the outer layer may each include four microlayers of electrospun PTFE filaments. Such microlayers are available as Bioweb® provided by Zeus Industrial Products, Inc., Orangeburg, S.C. Other examples of materials and microlayers may be used. With the use of microlayers, the reinforcement element and/or stent frame structure may be disposed between different microlayers or the same microlayers as described above.

A way to demonstrate the effectiveness of the reinforcement element embedded with the graft covering is through a tensile test. A tensile test was performed on four samples. The control sample comprises a tubular graft with a longitudinal length of 20 mm, and the graft comprising 8 Bioweb microlayers with the reinforcement element omitted. The first sample includes a tubular graft with a longitudinal length of 20 mm, and the graft comprising 4 Bioweb outer microlayers and 4 Bioweb inner microlayers, with a 0.46 mm coiled PET yarn (40 denier) of 40 mm (twice the graft length) disposed between the four outer and four inner layers. The second sample includes a tubular graft with a longitudinal length of 20 mm, and the graft comprising 4 Bioweb outer microlayers and 4 Bioweb inner microlayers, with a 0.46 mm coiled PET yarn (40 denier) of 80 mm (four times the graft length) disposed between the four outer and four inner layers. The third sample includes a tubular graft with a longitudinal length of 20 mm, and the graft comprising 4 Bioweb outer microlayers and 4 Bioweb inner microlayers, with a 0.46 mm linear PET yarn (40 denier) wrapped helically without any bends disposed between the four outer and four inner layers.

The amount of extension of the graft as a result of a tensile load axially applied to the tubular graft was measured until rupture. The control sample had the greatest extension capability (over 100%) prior to rupture but failed to resist mechanical loads, having the lowest load (about 1.5N) at 10 mm (50%) length of extension and the lowest load of 1.3 N at 50% length of extension. The third sample with a straight yarn (no bends) reinforced the mechanical strength of the device but the relative extension requirements of at least 50% were not met by rupturing at about 3.5N at below 8 mm (40%) length of extension. The covered stent reinforced with a straight yarn furthermore exhibited relative high bending stiffness. The first sample had the highest load (about 2.8N) at 10 mm (50%) length of extension. The second sample had the highest maximum load (about 3 N) at 20 mm (100%) length of extension. It was discovered that the desirable properties for the graft that is implanted within a body vessel should have the highest maximum loads up to 100% length of extensions. The graft material configured to withstand higher loads within this range of extension may be effective to control creep within the graft material and later creep rupture. The reinforcement element embedded within the graft covering as described herein is shown to bear creep and creep rupture, without losing longitudinal flexibility due to the added embedded element.

Figure 14:
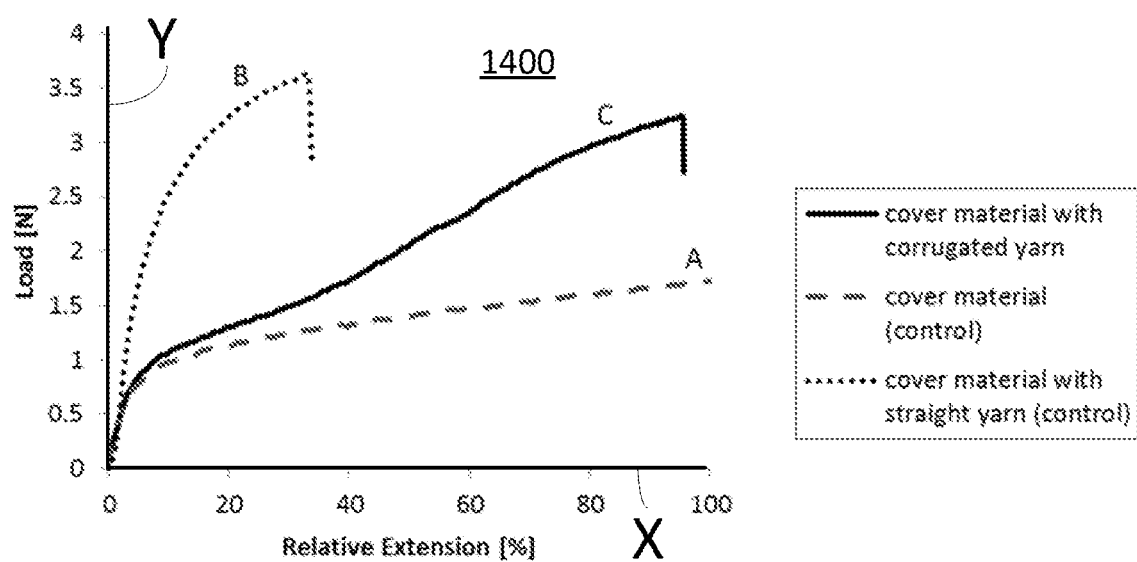
FIG. 14 is a graph depicting results of the medical device under a tensile test.

The graft material may be able to resist high loads, have relative extensions of a least 50%, and still have an extension margin before rupturing. FIG. 14 is a graph 1400 showing representative tensile test results of dog-bone shaped graft cover material with or without a PET yarn, 40 Denier as reinforcement element (gauge length: 20 mm). The x-axis X indicates the extension of the graft under tensile loading relative to its original length, and the y-axis Y indicates the amount of tensile load applied for the tensile test. Curve A (long dashed line) shows the graft with the reinforcement element omitted may be expanded to over 100% relative to its original length, and has low mechanical strength (less than 2N) relative to the others. Curve B (dotted line) shows the graft with a reinforcement PET element noncorrugated or nonbunched configuration, which provides suitable mechanical strength, the low relative extension (that is, the yarn ruptured at over 3.5N below 40% relative extension of its original length), and a relative high bending stiffness. Curve C (solid line) shows the graft with a reinforcement PET element in a corrugated or bunched configuration. The graft with the reinforcement PET element in a corrugated or bunched configuration may allow extension over 90% of its original length before the reinforcement element breaks at over 3N, suitable mechanical strength, and a relative low bending stiffness. The length of reinforcement PET element in the stretched conformation was 80 mm. Shorter lengths of the reinforcement element may result into higher slopes for loading but may rupture at a lower relative extension, and vice versa. To prevent creep rupture, the maximum relative extension of the reinforcement element, e.g. 50%, may be chosen in such a way to match the maximum overexpansion of the stent frame.

Figure 13A:
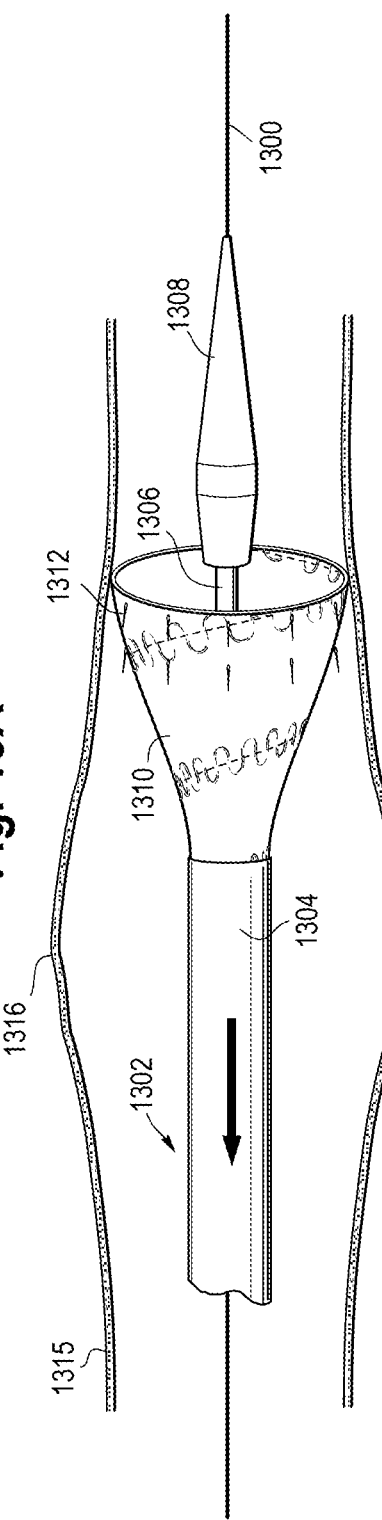
FIGS. 13A-13B depict a method of deploying a medical device with a reinforcement element for treatment of a body vessel wall.
Figure 13B:
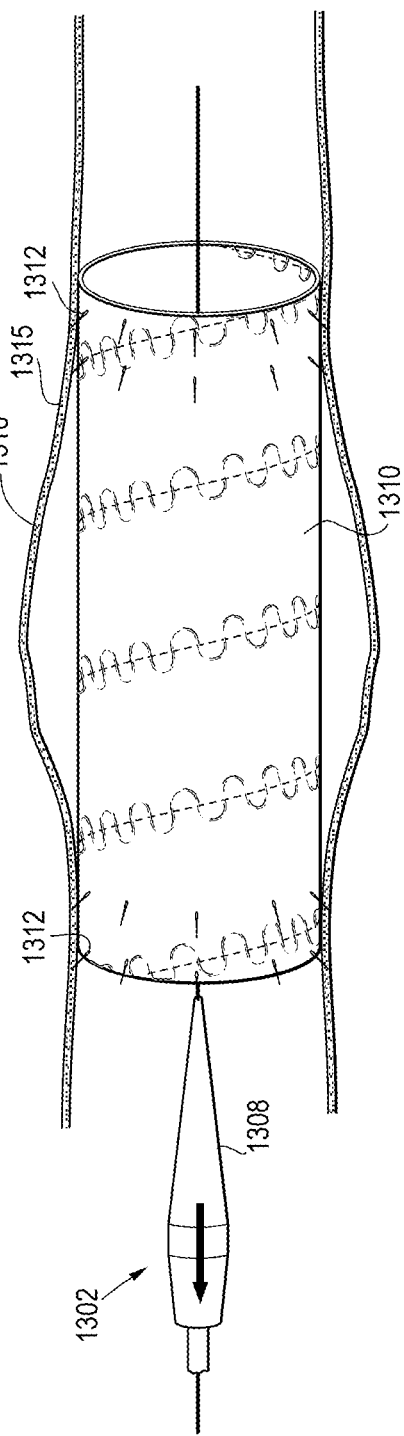

Methods of using any one of the medical devices described herein are contemplated, such as by placing a medical device described herein into a body at a point of treatment. Also, methods of using the medical devices described herein in combination with another medical device are contemplated, such as by placing a medical device described herein as a branch connecting stent within a fenestrated stent graft, and placing the medical devices together into a body at a point of treatment, such as a point of treatment in the aortic system. The medical device may be delivered with suitable techniques, depending on the type of medical device. In one example, access to the body may be attained by inserting an access device, such as an introducer sheath, into the body passageway. One typical procedure for inserting the introducer sheath over an inserted wire guide 1300 using the well-known Seldinger percutaneous entry technique. The medical device may be delivered with a stent deployment system 1302, as known, using the introducer sheath, and advanced to the treatment site, such as the aneurysm, typically using visual techniques such as fluoroscopy. The system 1302 may include one or more of the following: a retractable outer sheath 1304 radially disposed over an inner cannula 1306 and/or pusher device, as known. A nose cone dilator 1308 may be affixed to the proximal end of the inner cannula 1306 and the proximal end of the pusher device may be spaced from the nose cone dilator 1308 to define a retention region within the system. The medical device 1310, such as any one described herein, may be radially compressed to a lower profile for delivery and loaded onto the retention region. The outer sheath 1304 is moved relative to the loaded medical device 1310 to allow for radial expansion within the body, as shown in FIG. 13A. Trigger wires (not shown) may be provided and activated for removal of retention devices around the medical device and selective expansion of the medical device. The outer sheath 1304 is fully withdrawn from the medical device 1310 for implantation, generally with anchor or barbs 1312 into the body vessel wall 1315, spanning across the weakened portion 1316 of the body vessel wall 1315. Once implanted, the system may be removed from the body, as shown in FIG. 13B.

In one example, the medical device is a covered stent and the reinforcement element is a thin yarn, which may be foldable or bendable to exist in different conformational states. The reinforcement yarn embedded within the graft covering may provide different mechanical properties of the covered stent. The reinforcement yarn may provide the covered stent with greater longitudinal bending flexibility and/or limit creep and creep rupture potential.

In another example, the medical device may include a balloon expandable liner for use with balloon catheters. The balloon liner may be formed having the inner membrane layer and the outer membrane layer capturing the reinforcement element such as similarly shown in FIG. 2. The reinforcement element in the balloon liner includes the plurality of bends and is disposed about the pattern axis, such as similarly shown in FIG. 1. The reinforcement element may provide the balloon increased hoop strength to inhibit rupturing or bursting of the balloon. In addition to the materials described above in relation to the graft, the balloon membrane material may be any known balloon material, such as, for example, PEBAX, nylon, Hytrel, Arnitel or other polymers suitable for use. The balloon may also be compliant or non-compliant. Such balloons may be used for expanding balloon-expandable stents, angioplasty, or other body needs, as known in the art.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A prosthesis comprising:
a radially expandable stent frame structure;
a cover material disposed along the stent frame structure; and
a reinforcement element coupled to the cover material, the reinforcement element having a plurality of bends disposed about a pattern axis, the pattern axis arranged helically along the cover material,
wherein the cover material includes an outer layer disposed along an outer surface of the frame structure, and an inner layer disposed along an inner surface of the frame structure,
where the radially expandable stent frame structure comprises a plurality of stents that are axially disposed away from one another about a longitudinal axis of the cover material, such that the plurality of stents each form a closed shape when viewed in a direction substantially orthogonal relative to the main longitudinal axis of the cover material.

2. The prosthesis of claim 1, wherein the reinforcement element is embedded within the cover material.

3. The prosthesis of claim 2, wherein the stent frame structure is embedded within the cover material.

4. The prosthesis of claim 1, wherein at least one of the outer layer and the inner layer comprises a plurality of microlayers, and the reinforcement element is disposed between the microlayers.

5. The prosthesis of claim 1, wherein the reinforcement element is a single yarn.

6. The prosthesis of claim 1, wherein the prosthesis includes a proximal end and a distal end, wherein the reinforcement element in a stretched configuration without the plurality of bends has a longitudinal length at least twice a longitudinal length measured between the proximal and distal ends of the prosthesis.

7. The prosthesis of claim 1, wherein the plurality of bends of the reinforcement element is disposed generally in an undulating pattern about the pattern axis, wherein one of the plurality of bends forms each undulation of the undulating pattern.

8. The prosthesis of claim 1, wherein the plurality of bends of the reinforcement element is disposed generally in an undulating pattern about the pattern axis, wherein two or more of the plurality of bends form each undulation of the undulating pattern.

9. A prosthesis comprising:
a radially expandable stent frame structure;
a cover material disposed along the stent frame structure; and
a reinforcement element coupled to the cover material, the reinforcement element having a plurality of bends disposed about a pattern axis, the pattern axis arranged helically along the cover material,
wherein the cover material includes an outer layer disposed along an outer surface of the frame structure, and an inner layer disposed along an inner surface of the frame structure,
wherein the reinforcement element is embedded within the cover material.

10. The prosthesis of claim 9, wherein the stent frame structure is embedded within the cover material.

11. The prosthesis of claim 9, wherein the reinforcement element is a single yarn.

12. The prosthesis of claim 9, wherein the prosthesis includes a proximal end and a distal end, wherein the reinforcement element in a stretched configuration without the plurality of bends has a longitudinal length at least twice a longitudinal length measured between the proximal and distal ends of the prosthesis.

13. The prosthesis of claim 9, wherein the plurality of bends of the reinforcement element is disposed generally in an undulating pattern about the pattern axis, wherein one of the plurality of bends forms each undulation of the undulating pattern.

14. The prosthesis of claim 9, wherein the plurality of bends of the reinforcement element is disposed generally in an undulating pattern about the pattern axis, wherein two or more of the plurality of bends form each undulation of the undulating pattern.

15. A prosthesis comprising:
a radially expandable stent frame structure;
a cover material disposed along the stent frame structure; and
a reinforcement element coupled to the cover material, the reinforcement element having a plurality of bends disposed about a pattern axis, the pattern axis arranged helically along the cover material,
wherein the cover material includes an outer layer disposed along an outer surface of the frame structure, and an inner layer disposed along an inner surface of the frame structure,
wherein at least one of the outer layer and the inner layer comprises a plurality of microlayers, and the reinforcement element is disposed between the microlayers.

16. The prosthesis of claim 15, wherein the stent frame structure is embedded within the cover material.

17. The prosthesis of claim 15, wherein the reinforcement element is a single yarn.

18. The prosthesis of claim 15, wherein the prosthesis includes a proximal end and a distal end, wherein the reinforcement element in a stretched configuration without the plurality of bends has a longitudinal length at least twice a longitudinal length measured between the proximal and distal ends of the prosthesis.

19. The prosthesis of claim 15, wherein the plurality of bends of the reinforcement element is disposed generally in an undulating pattern about the pattern axis, wherein one of the plurality of bends forms each undulation of the undulating pattern.

20. The prosthesis of claim 15, wherein the plurality of bends of the reinforcement element is disposed generally in an undulating pattern about the pattern axis, wherein two or more of the plurality of bends form each undulation of the undulating pattern.

* * * * *